US011771316B2

(12) United States Patent
Kobayashi et al.

(10) Patent No.: US 11,771,316 B2
(45) Date of Patent: Oct. 3, 2023

(54) METHOD FOR OPHTHALMIC EXAMINATION AND REMOTE EXAMINATION PROGRAM

(71) Applicant: NIDEK CO., LTD., Aichi (JP)

(72) Inventors: Shirohisa Kobayashi, Aichi (JP); Kazunari Shimizu, Aichi (JP); Koji Hamaguchi, Aichi (JP); Miki Tomiyasu, Aichi (JP); Tsutomu Uemura, Aichi (JP)

(73) Assignee: NIDEK CO., LTD., Aichi (JP)

( * ) Notice: Subject to any disclaimer, the term of this patent is extended or adjusted under 35 U.S.C. 154(b) by 305 days.

(21) Appl. No.: 17/108,379

(22) Filed: Dec. 1, 2020

(65) Prior Publication Data

US 2021/0169323 A1 Jun. 10, 2021

(30) Foreign Application Priority Data

Dec. 4, 2019 (JP) .................................. 2019-219980

(51) Int. Cl.
*A61B 3/00* (2006.01)
*A61B 3/18* (2006.01)

(52) U.S. Cl.
CPC .......... *A61B 3/0033* (2013.01); *A61B 3/0041* (2013.01); *A61B 3/18* (2013.01)

(58) Field of Classification Search
CPC .... A61B 3/0016; A61B 3/0033; A61B 3/0041
(Continued)

(56) References Cited

U.S. PATENT DOCUMENTS

2010/0182565 A1* 7/2010 Reichow .................. A61H 5/00
351/203
2017/0027445 A1 2/2017 Isogai
(Continued)

FOREIGN PATENT DOCUMENTS

| JP | 2017-29369 A | 2/2017 |
| JP | 2017-102759 A | 6/2017 |
| JP | 2017-217122 A | 12/2017 |

OTHER PUBLICATIONS

Hartest Precision Instruments. (2009). Henson Visual Field Screeners Instruction Manual for the Henson 5000, 6000, and 7000. Redhill UK; Hartest Precision Instruments. (Year: 2009).*

*Primary Examiner* — Zachary W Wilkes
(74) *Attorney, Agent, or Firm* — Rankin, Hill & Clark LLP

(57) ABSTRACT

Provided is a method for an ophthalmic examination by an ophthalmic examination system including an ophthalmic examination apparatus and an examiner-side apparatus that is connected to the ophthalmic examination apparatus by a network and is provided with an interface for input/output, the method including: a transmission step of transmitting an error signal from the ophthalmic examination apparatus to the examiner-side apparatus upon occurrence of an error in the ophthalmic examination apparatus; a selection step of, upon the examiner-side apparatus receiving the error signal, notifying an examiner of the occurrence of the error via the interface and also accepting selection input for selecting any of a plurality of predetermined handling methods of the error; a response step of the examiner-side apparatus transmitting a response signal to the ophthalmic examination apparatus on the basis of the selection input; and a notification step of, upon the ophthalmic examination apparatus receiving the response signal, notifying the examinee of
(Continued)

guidance information on the action against the error on the basis of the response signal via an output device.

11 Claims, 6 Drawing Sheets

(58) Field of Classification Search
USPC .......................................................... 351/206
See application file for complete search history.

(56) References Cited

U.S. PATENT DOCUMENTS

2017/0347872 A1* 12/2017 Ozaki .................... A61B 3/152
2020/0337794 A1* 10/2020 Hall .......................... G06T 7/73

* cited by examiner

METHOD FOR OPHTHALMIC EXAMINATION AND REMOTE EXAMINATION PROGRAM

CROSS-REFERENCE TO RELATED APPLICATION

This application claims priority from Japanese Patent Application No. 2019-219980 filed with the Japan Patent Office on Dec. 4, 2019, the entire content of which is hereby incorporated by reference.

BACKGROUND

1. Technical Field

The present disclosure relates to a method for an ophthalmic examination and a remote examination program.

2. Related Art

In the ophthalmologic field, automated examination apparatuses are coming into widespread use. For example, JP-A-2017-217122 discloses an apparatus that operates automatically during a period of time from when an examinee places his/her face on the chin rest to when examinations for both eyes are complete.

Generally, various examinations can be conducted in facilities where ophthalmic examination apparatuses are installed. With the widespread use of the automated examination apparatuses, a system for allowing one examiner to take charge of a plurality of examinations or tasks at the same time is being studied. For example, a technology for allowing an examiner who handles a terminal apparatus connected to a plurality of ophthalmic examination apparatuses via a network to grasp operating states of the plurality of ophthalmic examination apparatuses via the terminal apparatus, and a technology for allowing the examiner to remotely operate the plurality of ophthalmic examination apparatuses via the terminal apparatus as needed have been proposed (refer to, for example, JP-A-2017-029369).

Moreover, one examinee may undergo a plurality of kinds of examinations in the facility in a day (refer to, for example, JP-A-2017-102759).

SUMMARY

A method for an ophthalmic examination according to the present embodiment is a method for an ophthalmic examination by an ophthalmic examination system including an ophthalmic examination apparatus and an examiner-side apparatus that is connected to the ophthalmic examination apparatus by a network and is provided with an interface for input/output, the method including: a transmission step of transmitting an error signal from the ophthalmic examination apparatus to the examiner-side apparatus upon occurrence of an error in the ophthalmic examination apparatus; a selection step of, upon the examiner-side apparatus receiving the error signal, notifying an examiner of the occurrence of the error via the interface and also accepting selection input for selecting any of a plurality of predetermined handling methods of the error; a response step of the examiner-side apparatus transmitting a response signal to the ophthalmic examination apparatus on the basis of the selection input; and a notification step of, upon the ophthalmic examination apparatus receiving the response signal, notifying the examinee of guidance information on the action against the error on the basis of the response signal via an output device.

DETAILED DESCRIPTION

Figure 1:
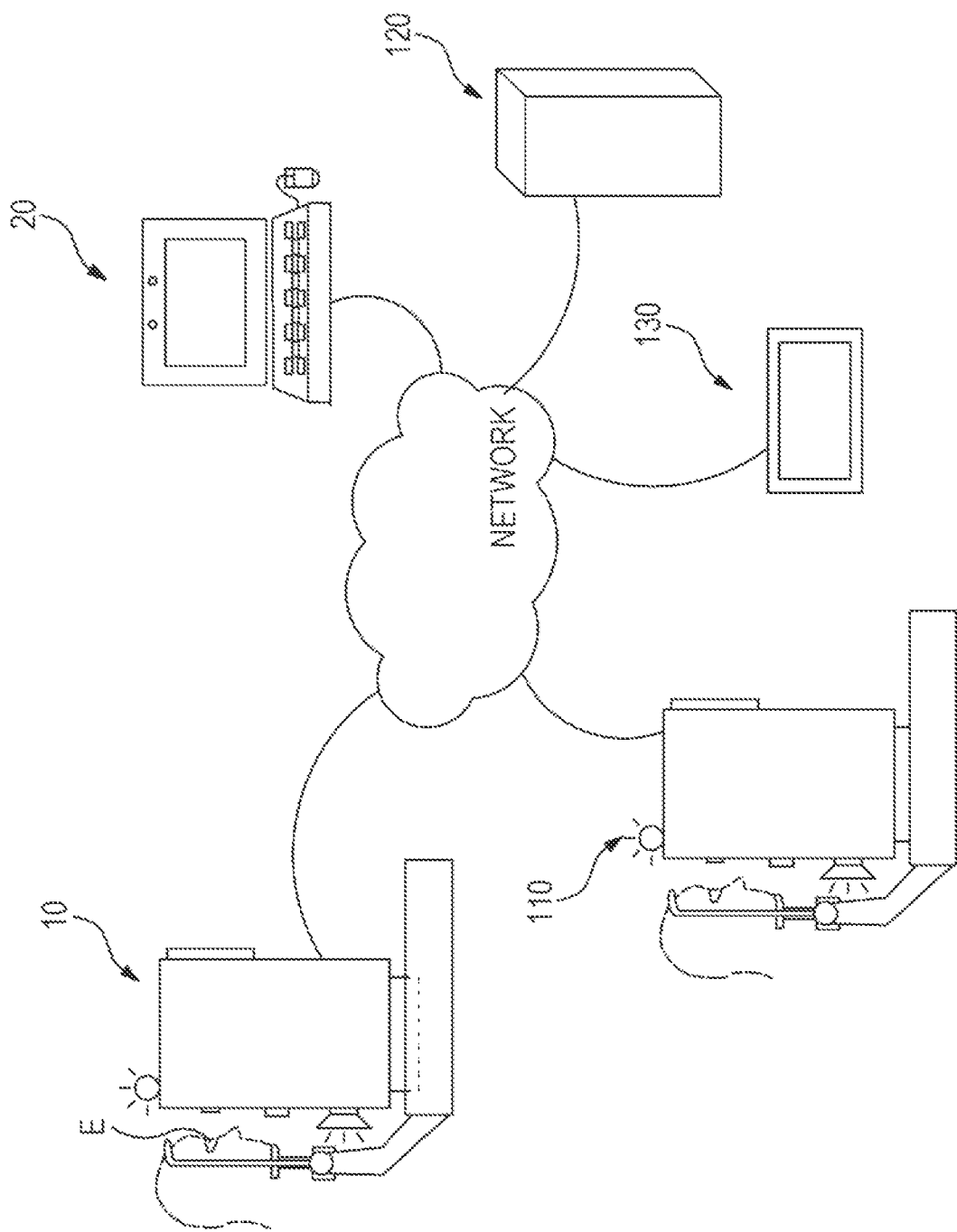
FIG. 1 is a diagram illustrating an outline of an ophthalmic examination system 1 according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Even if the automation of the ophthalmic examination apparatus progresses, there may be a case that requires the intervention of an examiner in an examination by the ophthalmic examination apparatus.

For example, an examination of an examinee's eye by the ophthalmic examination apparatus generally requires accurate alignment (alignment) with the ophthalmic examination apparatus. However, a case where alignment control over the ophthalmic examination apparatus cannot be completed for a long time, or a case where alignment is inaccurate, may arise due to various causes. Examples of the causes include causes such as the movement of the head of an examinee, unstable fixation, occurrence of a blink, and diseases in the optic media of the examinee's eye.

Moreover, for example, a case where the ophthalmic examination apparatus cannot acquire a sufficiently reliable examination result may arise due to various causes.

In such cases, it is desired to provide notification to the examiner and then for the examiner to intervene in an examination by the ophthalmic examination apparatus, for example, by the examiner operating the ophthalmic examination apparatus manually and assisting the examinee.

However, when intervention is required, if the examiner is simultaneously charged with a plurality of examinations or tasks, or is at a distant location, it is difficult to timely intervene. Hence, a case where the examinee has to keep waiting for intervention is assumed.

At this point in time, the examinee is likely to hold distrust or complaints of the ophthalmic examination apparatus and the examiner, which may result in a reduction in the examinee's compliance with the examination.

Moreover, if an examination for one examinee is prolonged due to the occurrence of an error, it is conceivable that influences such as an increase in the examination waiting time of another examinee and congested examinations are caused. In other words, the examination efficiency for all examination targets may be reduced.

The present disclosure has been made considering at least one of the problems of the known technologies. A technical issue of the present disclosure is to provide a method for an ophthalmic examination that allows an examiner to excellently intervene in an examination by an ophthalmic examination apparatus, and a remote examination program.

A method for an ophthalmic examination according to the first aspect is a method for an ophthalmic examination by an ophthalmic examination system including an ophthalmic examination apparatus and an examiner-side apparatus that is connected to the ophthalmic examination apparatus by a network and is provided with an interface for input/output, the method including: a transmission step of transmitting an error signal from the ophthalmic examination apparatus to the examiner-side apparatus upon occurrence of an error in the ophthalmic examination apparatus; a selection step of, upon the examiner-side apparatus receiving the error signal, notifying an examiner of the occurrence of the error via the interface and also accepting selection input for selecting any of a plurality of predetermined handling methods of the error; a response step of the examiner-side apparatus transmitting a response signal to the ophthalmic examination apparatus on the basis of the selection input; and a notification step of, upon the ophthalmic examination apparatus receiving the response signal, notifying the examinee of guidance information on the action against the error on the basis of the response signal via an output device.

The present disclosure is described below on the basis of an embodiment with reference to the drawings. The following headings categorized with < > can be used independently of, or related to, each other.

<Ophthalmic Examination System>

A method for an ophthalmic examination according to an embodiment is conducted by an ophthalmic examination system 1 illustrated by example in FIG. 1. The ophthalmic examination system 1 is used to examine (for example, measure the eye characteristics of or photograph) the eyes in medical institutions, venues for health examinations and screenings, and the like (hereinafter collectively referred to as a "facility").

The ophthalmic examination system 1 includes at least an ophthalmic examination apparatus 10 and an examiner-specific apparatus 20. Each apparatus included in the ophthalmic examination system 1 is connected by a network. Each apparatus can communicate each type of data such as an examination result, an image, audio, and a command with each other via the network. The ophthalmic examination apparatus 10 and the examiner-specific apparatus 20 are placed away from each other. The following description is given, assuming that both apparatuses are placed in different rooms in one facility, unless otherwise specified. However, the placement is not necessarily limited to this. Both apparatuses may be placed away from each other in one laboratory, or may be placed in different facilities.

<Ophthalmic Examination Apparatus>

The ophthalmic examination apparatus 10 has a configuration suitable for an automatic examination of an examinee's eye. As an example, the ophthalmic examination apparatus 10 may include at least an ophthalmic examination unit 11, an alignment driving unit 12, a detection unit 13, and a controller 14 as illustrated in FIG. 1.

The ophthalmic examination unit 11 includes a measuring system or photographing system for examining (for example, measuring the eye characteristics of or photographing) the examinee's eye. An examination by the ophthalmic examination apparatus 10 may be an objective examination. In this case, the ophthalmic examination unit 11 is provided with a detector for obtaining an examination result. An examination result is acquired on the basis of a signal from the detector. Moreover, the examination by the ophthalmic examination apparatus 10 may be a subjective examination. In this case, the ophthalmic examination apparatus 10 includes an input unit (not illustrated) for inputting a response from the examinee. An examination result of the subjective examination is acquired on the basis of the input result.

The alignment driving unit 12 adjusts a positional relationship between the examinee's eye and the ophthalmic examination unit 11. The alignment driving unit 12 may move the ophthalmic examination unit 11, or move the position of the face of the examinee, or move both. The detection unit 13 detects a positional relationship (also called an alignment state) between the examinee's eye and the ophthalmic examination unit 11.

The controller 14 is a computer that controls the operation of each unit of the ophthalmic examination apparatus 10. The controller 14 may include a processor (for example, a CPU) and various types of memory. The processor executes an automatic ophthalmic examination program to cause the ophthalmic examination apparatus 10 to conduct an examination on the examinee's eye. Consequently, in the ophthalmic examination apparatus 10, the drive of the alignment driving unit 12 is controlled on the basis of the alignment state detected by the detection unit 13, an appropriate alignment state is obtained, and then measurement or photographing is executed automatically. The automatic ophthalmic examination program is stored in memory accessible from the processor. The program may be prestored in, for example, the internal memory of the controller 14.

As an example, the ophthalmic examination apparatus 10 may include a face support unit 15, a monitor 16, a speaker 17, a microphone 18, and an operation input unit 19 as illustrated in FIG. 1, in addition to the above configuration. The monitor 16 and the speaker 17 are examples of output devices. The output devices are used to notify the examinee of information. The output devices are not required to be previously provided to the ophthalmic examination apparatus 10 and may be separate from the ophthalmic examination apparatus 10. Moreover, the ophthalmic examination apparatus 10 may further include various unillustrated sensors.

<Regarding Modality of Ophthalmic Examination Apparatus>

The ophthalmic examination apparatus 10 may be any of various modalities. Examples of the ophthalmic examination apparatus 10 may include apparatuses that measures the refractive characteristics of the examinee's eye (for example, a refractometer, a wavefront sensor, a keratometer, and a topography), an eye pressure measurement apparatus (a tonometer), an ocular axial length measurement apparatus, a corneal endothelial cell measurement apparatus (a specular microscope), an anterior chamber angle photographing apparatus (a goniometer), a fundus photographing apparatus (a fundus camera, a scanning fundus photographing apparatus, an optical coherence tomography, and the like), and others. The ophthalmic examination apparatus 10 may be a complex apparatus that can conduct examinations related to a plurality of modalities.

<Examiner-Specific Apparatus>

The examiner-specific apparatus 20 is used to allow the examiner to remotely intervene in the examination by the ophthalmic examination apparatus 10. In the present disclosure, the operation of the ophthalmic examination apparatus 10, and assistance in the examination by the ophthalmic examination apparatus 10 are collectively referred to as "intervention".

Figure 3:
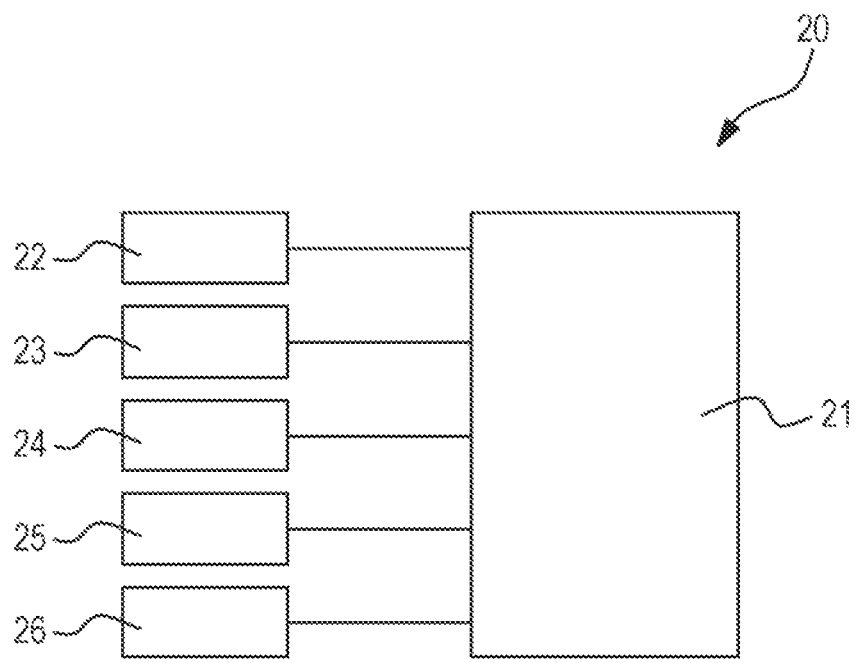
FIG. 3 is a block diagram for explaining a rough configuration of an examiner-side apparatus 20.

The examiner-specific apparatus 20 is a computer that accepts signals from the ophthalmic examination apparatus 10 and operation input by the examiner, and performs various processes. The examiner-specific apparatus 20 may be a general-purpose computer such as a PC or a tablet computer. A processor (not illustrated) of the examiner-specific apparatus 20 executes the remote examination program to execute various processes (refer to a flowchart of FIG. 4) necessary to intervene in an examination. The remote examination program is stored in memory accessible by the processor of the examiner-specific apparatus 20. This may be prestored in, for example, internal memory of the examiner-specific apparatus 20. A block diagram of FIG. 3 illustrates a rough configuration of the examiner-specific apparatus 20 as an example. A unit including the processor and the internal memory is illustrated as a main body unit 21 in FIG. 3.

The examiner-specific apparatus 20 includes an interface for input/output. The examiner can intervene in an examination via the interface. For example, a monitor 22, a speaker 23, a camera 24, a microphone 25, and an operation input unit 26 may be included as the interfaces for input/output as illustrated in FIG. 3.

The examiner-specific apparatus 20 receives various types of information transmitted by the ophthalmic examination apparatus 10 via the network. The examiner-specific apparatus 20 notifies the examiner of the received information via the interface for input/output. For example, various images (for example, observation images of the eye) taken by the ophthalmic examination apparatus 10 may be received. In this case, various images may be displayed on the monitor 22. Moreover, a result of an examination by the ophthalmic examination apparatus 10 may be received. In this case, information indicating the examination result may be displayed on the monitor 22. Moreover, an error signal occurring in the ophthalmic examination apparatus 10 may be received. Information indicating the occurrence of the error may be outputted to the examiner via at least one of the monitor 22 and the speaker 23. A process at the time of the occurrence of an error is described in detail below.

The examiner can intervene in an examination at appropriate times on the basis of various types of information grasped via the interface for input/output. The intervention using the examiner-specific apparatus 20 can take various forms. For example, the examiner may use the examiner-specific apparatus 20 to assist by operating the ophthalmic examination apparatus 10, or by providing an instruction to the examinee, and accordingly intervene in an examination. The examiner-specific apparatus 20 may be configured in such a manner that any of a plurality of predetermined intervention forms can be selected by operating the interface for input/output.

The configuration is not limited to this. If the examiner judges that intervention is required, the examiner may move to a place where the examination is being conducted, and intervene in the examination by assisting in opening the eyelids, supporting the examinee's head to keep still, or operating the ophthalmic examination apparatus 10.

<Additional Configuration in Ophthalmic Examination System>

Moreover, the ophthalmic examination system 1 according to an embodiment may include one or more of the following apparatuses:

<Second Ophthalmic Examination Apparatus>

The ophthalmic examination system 1 may include one or more second ophthalmic examination apparatuses (an ophthalmic examination apparatus 110 in FIG. 1) in addition to the ophthalmic examination apparatus 10. The second ophthalmic examination apparatus 110 may be an apparatus of a modality different from the ophthalmic examination apparatus 10, or an apparatus of the same modality. The second ophthalmic examination apparatus 110 may include at least configurations suitable for the automation of an examination (for example, an ophthalmic examination unit, an alignment driving unit, a detection unit, and a controller) (none is illustrated) as in the ophthalmic examination apparatus 10.

Moreover, the examiner-specific apparatus 20 may be configured in such a manner as to be capable of receiving various types of information (at least any of, for example, various images, an examination result, and an error signal) transmitted from the second ophthalmic examination apparatus 110. The examiner-specific apparatus 20 receives various types of information transmitted by the ophthalmic examination apparatus 10 via the network. The examiner-specific apparatus 20 notifies the examiner of the received information via the interface for input/output.

<Operator-Specific Terminal Apparatus>

As illustrated in FIG. 1, the ophthalmic examination system 1 may include an operator-specific terminal apparatus (hereinafter simply abbreviated as a terminal apparatus) 130. The terminal apparatus 130 is used to notify an operator of the examiner's instruction. The terminal apparatus 130 may be a mobile computer terminal (for example, a PDA, a tablet computer, a smartphone, or a wearable computer) that can be carried by the operator. For example, an operator who is away from the ophthalmic examination apparatus 10 is instructed to move to the place of the ophthalmic examination apparatus 10 and assist in an examination.

The operator may be a person who has a skill in directly assisting an examinee by, for example, opening the eyelids and supporting the examinee's head to keep still. Moreover, the operator may be a second examiner who has a skill in operating the ophthalmic examination apparatus 10 manually. The examiner may not be able to intervene immediately and appropriately in an examination by the ophthalmic examination apparatus 10 due to various circumstances such as that the examiner is at a distant location from the ophthalmic examination apparatus 10, that the examiner is working on another task, and that the ophthalmic examination system 1 does not support remote operation. In this case, the examiner's instruction to the operator through the examiner-specific apparatus 20 and the terminal apparatus 130 is considered to be useful.

<Management Apparatus>

As illustrated in FIG. 1, the ophthalmic examination system 1 may include a management apparatus 120. The management apparatus 120 may manage examination items and progress (statuses) of a plurality of examinations conducted on each examinee in a day. Moreover, the management apparatus 120 may manage the (items and) order of examinations that an examinee undergoes for each examinee. Information managed by the management apparatus 120 is outputted to a terminal apparatus placed at each location in the facility. The terminal apparatus may be placed at a location where an examination is conducted, or carried by an operator or examinee in the facility (for example, the terminal apparatus 130). For example, examination items for each examinee, the name of an examinee who undergoes an examination next, and scheduled time when each examinee undergoes an examination may be outputted to the terminal apparatus. The information outputted to the terminal apparatus may be used to guide and lead an examinee in the facility.

The information managed by the management apparatus 120 may be updated in substantially real time and outputted to the terminal apparatus whenever necessary. For example, the management apparatus associates any of a plurality of statuses such as "not started", "in progress", and "completed" with each examination item of each examinee. The status to be associated is changed on the basis of a signal from a terminal apparatus prepared for each examination.

For example, an acceptance step performed prior to each examination may switch the status from "not started" to "in progress". In the acceptance step, an examinee and an examination item that the examinee undergoes next are identified. The examinee is identified by a terminal apparatus prepared for each examination. Accordingly, the examinee and the examination item are identified. For example, a storage medium for ID authentication (for example, a barcode, an RFID tag, or a magnetic card) carried by the examinee may be read by the terminal apparatus to identify the examinee. Moreover, a biometric authentication technology may be used to identify the examinee. Moreover, the ID of the examinee who will undergo the examination now may be inputted or selected manually in the terminal apparatus to identify the examinee.

Moreover, for example, switching from "in progress" to "completed" may be performed on the basis of an examination complete signal from the examination apparatus. Moreover, for example, if the location of the examinee in the facility can be detected, the status may be switched from "in progress" to "completed" on the basis of the detection of the movement of the examinee from a place where an examination of each item is conducted to another place. The method for detecting the location of the examinee can include various methods. For example, an indoor GPS may be used, or RFID may be used, or a video camera installed at each location in the facility may be used. In this case, an apparatus that detects the location of the examinee can be used as the terminal apparatus. Moreover, the status switching operation may be inputted or selected manually in the terminal apparatus.

<Description of Operation>

Figure 4:
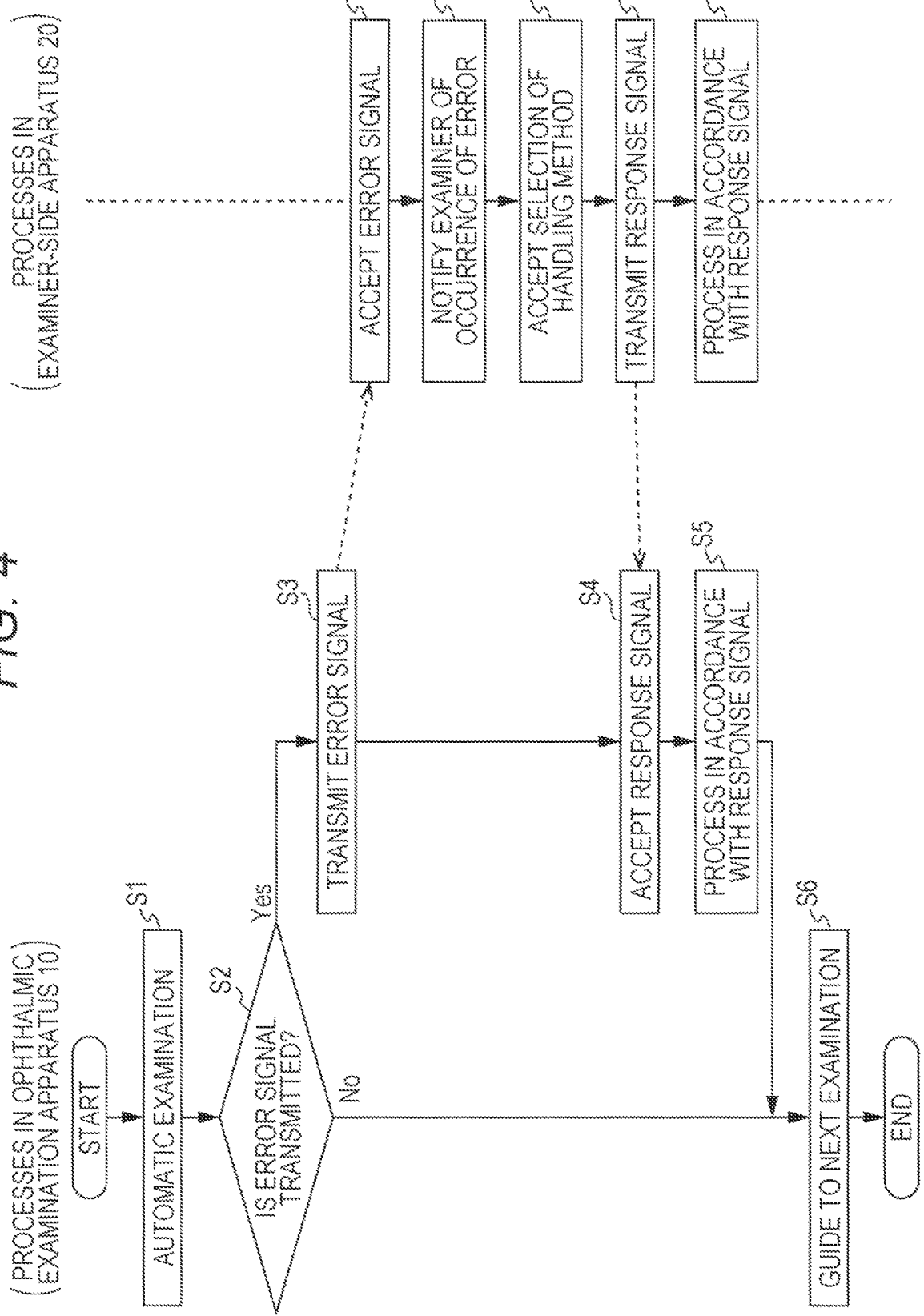
FIG. 4 is a flowchart illustrating an automatic examination program by the ophthalmic examination apparatus 10 and a remote examination program by the examiner-side apparatus 20.

Next, the use pattern of the ophthalmic examination system 1 is described with reference to the flowchart of FIG. 4.

<Start of Examination>

Upon the examination, the examinee is guided in such a manner that the face support unit 15 of the ophthalmic examination apparatus 10 supports the face of the examinee. The posture of the examinee is adjusted in such a manner that the chin and the forehead of the examinee touch the chin rest and the forehead rest of the face support unit 15, respectively. The guidance may be conducted by the examiner or operator, or by the ophthalmic examination system 1.

The ophthalmic examination apparatus 10 starts the examination on the basis of a predetermined trigger. The trigger may be the detection of the examinee's eye by the ophthalmic examination apparatus 10 at a predetermined position, or predetermined operation input into the ophthalmic examination apparatus 10 or terminal apparatus.

<Automatic Examination Step>

After the occurrence of the trigger, the ophthalmic examination apparatus 10 executes an automatic examination step (S1). As illustrated in FIG. 1, the automatic examination step is broadly divided into automatic alignment and automatic measurement or photographing of the examinee's eye.

In the automatic alignment, the controller 14 controls the alignment driving unit 12 in such a manner that the positional relationship between the examinee's eye and the examination unit 11, which is detected by the detection unit 13, is adjusted to a predetermined positional relationship (within an alignment permissible range). Moreover, after the adjustment of the positional relationship by the automatic alignment, the controller 14 controls the ophthalmic examination unit 11, and measures or photographs the examinee's eye. Please refer to, for example, the contents described in JP-A-2017-217122 mentioned above for more details about the automatic examination step.

In the automatic examination step, at least any of an observation image and an examination result, which is acquired by the ophthalmic examination apparatus 10, is transmitted to the examiner-side apparatus 20 whenever necessary.

<Determination Step>

In the ophthalmic examination apparatus 10, whether or not to transmit (process) an error signal is determined (S2). If the transmission of an error signal is not necessary, the examination is ended. The determination is made appropriately when the occurrence of an error is detected. The occurrence of an error may be detected on the basis of, for example, information outputted from the examination unit 11 and the detection unit 13. Moreover, the occurrence of an error may be detected on the basis of a detection signal from an unillustrated sensor provided to the ophthalmic examination apparatus 10. At this point in time, the occurrence of errors of various types may be detected. The occurrence of, for example, an alignment error and a measurement error may be detected.

The occurrence of an alignment error may be detected in at least any of, for example, the cases listed below:

It has been detected that the face was moved away from the face support unit 15.

The contact of the face with the examination unit 11 has been detected.

The detection unit 13 could not detect the position of the examinee's eye.

Even after the passage of a predetermined period of time, the positional relationship between the examinee's eye and the examination unit 11 could not be adjusted in such a manner as to fall within the alignment permissible range.

Moreover, the occurrence of a measurement error may be detected in at least any of, for example, the cases listed below:

A blink has been detected at the timing of measurement or photographing by the ophthalmic examination unit 11.

A sufficiently reliable examination result could not be obtained due to microcoria, a disease, or the like.

(It is presumed that) a measurement result is beyond a measurable range of the ophthalmic examination unit 11.

<Transmission Step>

When an error occurs in any of alignment control and the measurement or photographing of the examinee's eye, a transmission process (transmission step) is executed in the ophthalmic examination apparatus 10 (S3). Consequently, an error signal is transmitted from the ophthalmic examination apparatus 10 to the examiner-side apparatus 20.

As an example, if it is determined in the prior determination process (the determination step; S2) that it is necessary to transmit (process) an error signal (S2; No) in the flowchart of FIG. 4, the transmission process is executed. In the transmission process, an error signal is transmitted to the examiner-side apparatus 20. The examiner is requested through the examiner-side apparatus 20 to intervene in the examination on the basis of the transmission of the error signal.

The error signal may include information indicating the content of the error. For example, the error signal may include information that identifies an operation stage, where the error has occurred, of the ophthalmic examination apparatus 10 in the examination. As a specific example, information that differentiates between the above alignment and measurement errors may be included. Moreover, for example, the error signal may include information that identifies the cause of the error. As a specific example, information that differentiates some error occurrence cases exemplified above may be included.

The error signal transmission process is not necessarily required to be performed whenever the occurrence of an error is detected. For example, the controller 14 may retry an operation that is being executed by the apparatus when the occurrence of the error is detected up to a predetermined number of times (after returning to a certain operation stage). If the error is still detected after the predetermined number of retries, the transmission process may be executed. In this case, the frequency of the occurrence of intervention in the examination by the ophthalmic examination apparatus 10 is reduced. As a result, for example, a burden on the examiner is reduced.

Moreover, if the ophthalmic examination apparatus 10 determines that it is necessary to transmit an error signal (S2: Yes), the controller 14 stops the operation of the ophthalmic examination apparatus 10. Moreover, at least any of information to the effect that the error has occurred, information to the effect that the examination is being suspended, and information to the effect that an action against the error is being requested may be notified via output devices (for example, the monitor 16 and the speaker 17).

Moreover, the examinee who has received the notification of the occurrence of the error and the suspension of the examination may feel anxious and leave the ophthalmic examination apparatus 10. If the examinee leaves the spot, it becomes difficult for the examiner to take an action against the error. Hence, in the embodiment, a notification that prompts the examinee to stay on the spot until a response is given from the examiner, or the operator other than the examiner, together with the above notification, may be provided via the output device.

<Selection Step>

The examiner-side apparatus 20 accepts the error signal (S11) and, in this case executes a selection step. In FIG. 4, S12 and S13 correspond to the selection step. In the selection step, the examiner-side apparatus 20 notifies the examiner of the occurrence of the error via the interfaces for input/output (for example, the monitor 22 and the speaker 23) (S12).

If the error signal includes, for example, information that identifies an operation stage where the error occurred, a notification of the operation stage may be provided concurrently with the occurrence of the error. Moreover, if the error signal includes, for example, information that identifies the cause of the error, a notification of the cause may be provided. In this manner, the examiner is notified of the content of the error concurrently with the occurrence of the error, which facilitates the examiner selecting an appropriate action.

Moreover, in the selection step, the examiner-side apparatus 20 further causes the examiner to select any of a plurality of predetermined error handling methods via the interface for input/output. In other words, the examiner-side apparatus 20 accepts a selection operation for selecting any of the predetermined error handling methods via the interface (S13).

<Response Step>

The examiner-side apparatus 20 transmits a response signal to the ophthalmic examination apparatus 10 on the basis of the handling method selection input in the selection step (S14). The response signal may include information for identifying the selected handling method. After the transmission of the response signal, control in accordance with the content of the response signal is performed in the ophthalmic examination apparatus 10 and the examiner-side apparatus 20 (S5 and S15).

<Specific Examples of Various Handling Methods>

Figure 5:
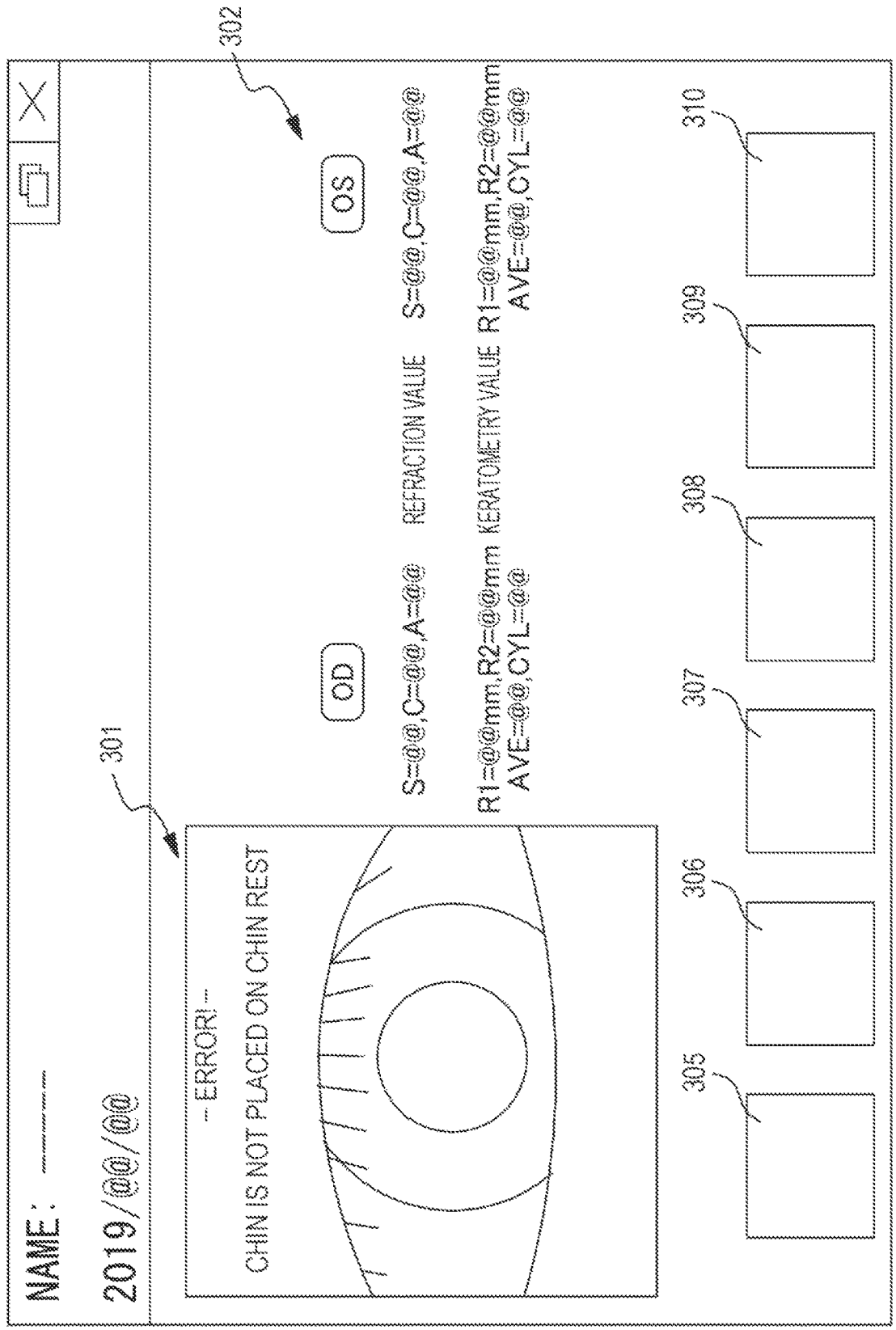
FIG. 5 is a diagram illustrating a remote examination screen.

Specific examples of the handling methods are described here, illustrating, in FIG. 5, an example of a screen configuration displayed on the monitor 22 of the examiner-side apparatus 20 upon an examination. A screen illustrated in FIG. 5 is hereinafter referred to as the remote examination screen. The remote examination screen is displayed in correspondence with an examination by the ophthalmic examination apparatus 10. The remote examination screen is displayed at least at the stage of having received an error signal. Naturally, the display may be able to be provided at an earlier stage (for example, at the start of the examination).

An observation image display area 301 where an observation image acquired by the ophthalmic examination apparatus 10 is displayed may be formed on the remote examination screen. Moreover, a result display area 302 where a result of the examination by the ophthalmic examination apparatus 10 is displayed may be formed.

If an error signal is received, display indicating the occurrence of the error is provided on the remote examination screen. For example, text indicating the occurrence of the error and the content of the error may be displayed on the screen as illustrated in FIG. 5. In FIG. 5, the text is displayed on the observation image, which facilitates the examiner who has been observing the observation image closely recognizing the occurrence of the error immediately. However, the display indicating the error may be provided at a position away from the observation image.

Moreover, various GUI widgets are displayed on the remote examination screen. As illustrated in FIG. 5, the GUI widgets may include a widget that is operated to select an error handling method. For example, buttons 306 to 309 are provided as examples of such widgets on the remote operation screen illustrated in FIG. 5, respectively for corresponding handling methods. If being notified of the occurrence of the error, the examiner can take an action in accordance with the operated button by performing a selection operation on one or more buttons. At this point in time, a response signal is transmitted from the examiner-side apparatus 20 to the ophthalmic examination apparatus 10 on the basis of the button selection operation.

<Call>

Figure 2:
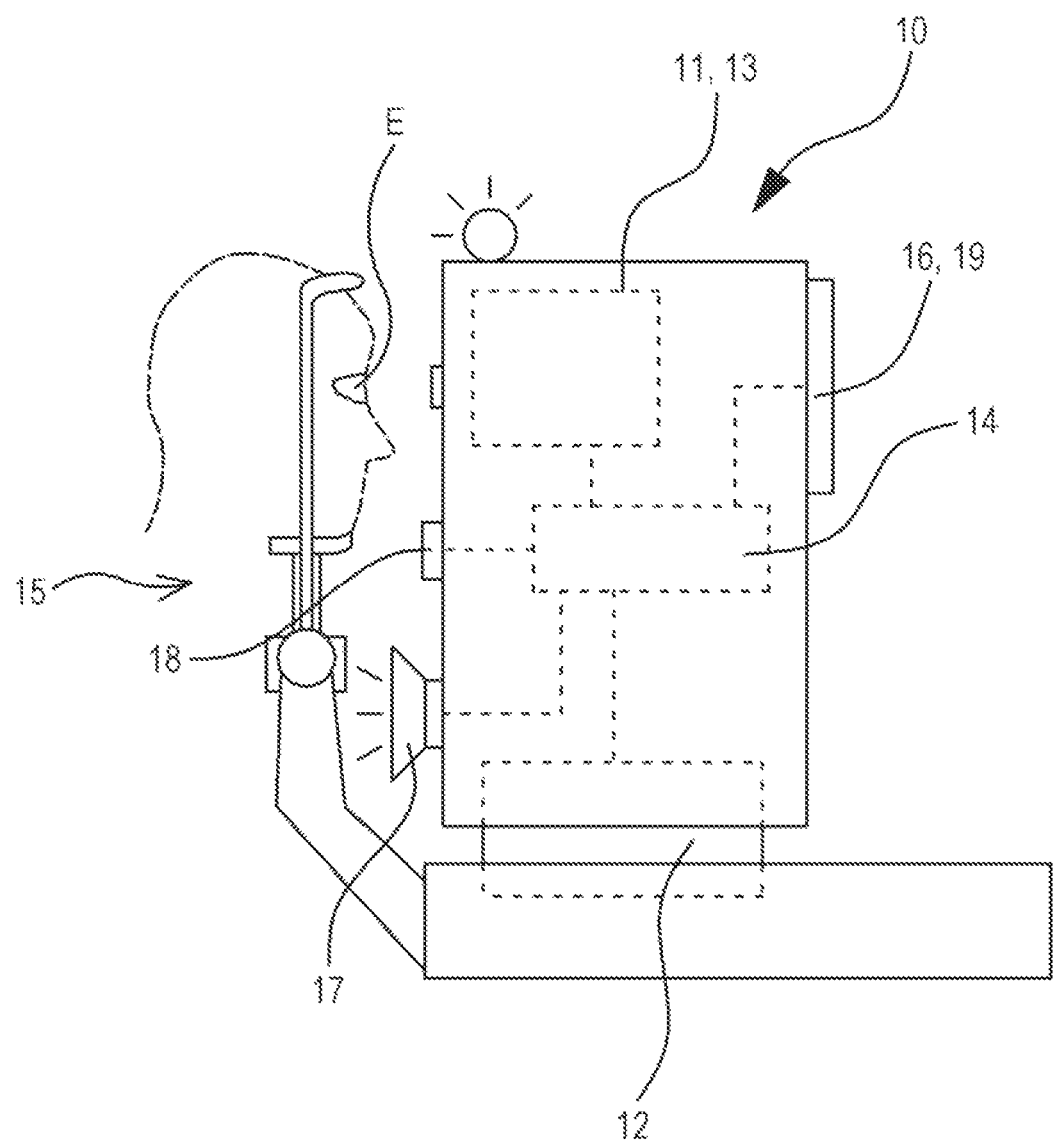
FIG. 2 is a schematic diagram for explaining a rough configuration of an ophthalmic examination apparatus 10.

In the embodiment, when a handling method is selected, a call (or a video call) may be able to be made between the examiner and the examinee. For example, a call may be started by operating a button 305 on the remote operation screen. In this case, a call can be made between the examiner and the examinee via the microphone 25 and the speaker 23 of the examiner-side apparatus 20 and the microphone 18 and the speaker 17 of the ophthalmic examination apparatus 10. If a video call is made, the face of the examiner which is photographed by the camera 24 of the examiner-side apparatus 20 is further shown on the monitor 16 on the ophthalmic examination apparatus 10 side. In FIGS. 1 and 2, the monitor 16 of the ophthalmic examination apparatus 10 is illustrated, setting the side opposite to the examinee as the front. For example, a mechanism for pointing the front toward the examinee at will may be provided.

At the time of the occurrence of an error, it is likely to reduce the examinee's anxiety by the examiner addressing the examinee immediately. Moreover, in, for example, a case where an error is occurring due to the eyelid opening or posture of the examinee, the examiner gives advice to the examinee; accordingly, the cause of the error can be easily solved. Furthermore, a call between the examiner and the examinee also allows the examiner to pry information that cannot be found out from the remote operation screen, which facilitates the selection of an appropriate action against the error.

<Specific Examples of Handling Methods>

Examples of a plurality of handling methods that can be selected at the time of the occurrence of an error include handling methods listed below. Any combination of the listed handling methods may be selectable, or other handling methods may be included.

Retry the automatic examination
Remote operation
Wait
Contact the operator
Stop (skip) the examination <Retry Automatic Examination>

When the automatic examination is retried, the button 306 on the remote operation screen is operated. The operation of the button 306 allows outputting, to the ophthalmic examination apparatus 10, a response signal for causing the ophthalmic examination apparatus 10 to re-execute the automatic examination. The ophthalmic examination apparatus 10 may re-execute the automatic examination on the basis of the response signal.

If the error was successfully handled due to, for example, the examiner's advice to the examinee by call, and if it can be confirmed through a call or the like that after the occurrence of the error, the examinee has found the cause of the error and is handling the error by himself/herself, it is desirable to operate the button 305 from the viewpoint of reducing a burden on the examiner.

<Remote Operation>

When a remote operation is performed, the button 307 on the remote operation screen is operated. The operation of the button 307 allows outputting a response signal to the effect of starting the remote operation to the ophthalmic examination apparatus 10. The control mode of the ophthalmic examination apparatus 10 may be switched from an automatic examination mode to a remote operation mode on the basis of the response signal. The ophthalmic examination apparatus 10 may be able to be driven on the basis of various control signals related to the remote operation via the examiner-side apparatus 20, in response to the switching to the remote operation mode. The remote operation is useful, for example, if it is difficult to detect alignment, and if it is difficult to find measurement or photographing timing due to pathological nystagmus.

There may be a case where the apparatus exhibits behavior different from one during the automatic examination after the transition from the automatic examination to the remote operation. In the remote operation, it is difficult for the examinee to grasp a state where the examiner is operating the apparatus. Hence, with the change of the behavior of the apparatus, it is likely to surprise the examinee and make the examinee anxious. In contrast, in the embodiment, when the ophthalmic examination apparatus 10 receives the response signal to the effect of starting the remote operation, the examinee may be notified of the information to the effect of starting the remote examination through the monitor 16 or the speaker 17. Consequently, even if the apparatus exhibits behavior different from one at the time of the automatic examination after the transition to the remote operation, it does not surprise the examinee so that it is unlikely to make the examinee anxious.

<Waiting Request>

If the examiner is desired to wait where he/she is for a while, the button 308 on the remote operation screen is operated. For example, the examinee may be made to wait for a period of time from the occurrence of the error to the manual operation of the ophthalmic examination apparatus 10. The operation of the button 308 allows outputting a response signal for prompting the examinee to wait to the ophthalmic examination apparatus 10. The ophthalmic examination apparatus 10 notifies the examinee of guidance information for prompting to wait on the basis of the response signal via the output devices (for example, the monitor 16 and the speaker 17). As a specific example, the examinee may be notified of, for example, a message saying "It will take you some time to be served. Please wait." via the output device. Moreover, if the button 308 for waiting is operated without selecting the button 305 for a call after the occurrence of the error, a notification indicating that the examiner has confirmed the occurrence of the error may be given together with the notification prompting to wait. The notification indicating that the examiner has confirmed the occurrence of the error is given; accordingly, the examiner's anxiety can be further reduced.

The guidance information prompting to wait is notified; accordingly, it is possible to make the examinee stay on the spot. This is useful, for example, if the examiner cannot take action immediately for reasons such as that the examiner is working on another task and that the examiner is in a different room, on a different floor, or in a different facility. Moreover, this is useful, for example, if the examiner and the operator other than the examiner need to move to the place of the ophthalmic examination apparatus 10 and directly assist the examination of the examinee.

<Contact Operator>

If it is desired to contact the operator who is away from the ophthalmic examination apparatus 10, the button 309 on the remote operation screen is operated. The operation of the button 309 may allow transmitting a response signal for contact to the operator-specific terminal apparatus 130. Consequently, the ophthalmic examination apparatus 10 may output, for example, a notification of a request to assist the examination to the operator via the operator-specific terminal apparatus 130. This action is useful if the examiner cannot take action immediately and there is an operator having an examination assisting skill in a facility where the ophthalmic examination apparatus 10 is placed.

Furthermore, if the button 309 is operated, it may also be able to select the content of a task that the operator is requested via the interface for input/output on the examiner-side apparatus 20. For example, a widget for accepting the operation of selecting a task content may be displayed on the monitor 22 of the examiner-side apparatus 20. If a task content is selected, a signal including information identifying the task content may be transmitted from the examiner-side apparatus 20 to the operator-specific terminal apparatus 130. The operator-specific terminal apparatus 130 outputs a notification of the task content to the operator on the basis of the received signal. Consequently, the operator can work on the task smoothly after moving to the place of the ophthalmic examination apparatus 10.

Moreover, the operation of the button 309 may also allow requesting the terminal apparatus 130 to start a call between the examiner-side apparatus 20 and the operator-specific terminal apparatus 130. In this case, the examiner can contact the operator verbally regarding a request of assistance and the content of assistance.

A response signal based on the selection operation of the button 309 may also be transmitted to the ophthalmic examination apparatus 10. Consequently, the examinee may be notified of, for example, the above guidance information for prompting to wait.

<Stop (Suspension) of Examination>

If it is desired to stop the examination, a stop button 310 is operated. The operation of the button 310 allows transmitting a response signal that instructs stop of the examination to the ophthalmic examination apparatus 10. The ophthalmic examination apparatus 10 stops the examination on the basis of the response signal. At this point in time, the state of the apparatus may be reset (initialized). Moreover, the examinee may be notified of information to the effect of stopping the examination via the output device. An action to stop the examination is useful if the examiner cannot take action immediately. This is especially useful if it takes approximately several minutes or more before an action is taken. If the examination is stopped, the examination by the ophthalmic examination apparatus 10 may be conducted again after another examination for the examinee is finished. It is desirable that the examiner and the operator be prepared in advance to intervene in the reexamination whenever necessary.

Moreover, guidance information for guiding the examinee to the next examination (a second examination) may be outputted via the output device on the basis of the response signal that instructs the stop of the examination. For example, a message and a figure, which indicate, for example, an examination item name of the next examination and how to go to the place to undergo the examination may be outputted as the guidance information via the output device.

<End of Examination>

If a manual measurement is complete, and if it is not determined in the determination step that the transmission (processing) of an error signal is required, the examination result is saved and the examination by the ophthalmic examination apparatus 10 is ended. At the end, the ophthalmic examination apparatus 10 may make a voice announcement for informing the examinee of the end of the examination. Moreover, at the end, the ophthalmic examination apparatus 10 may guide the examinee to the next destination (S6).

As described above, according to the embodiment, a response to the occurrence of an error can be made by selecting any of the plurality of predetermined handling methods. For example, even if the examiner is working on another task, it becomes easier to make a quick response. Consequently, it is possible to prevent a reduction in the efficiency of an examination due to the occurrence of an error in the facility. Furthermore, it is possible to prevent generation of distrust and anxiety about the apparatus or facility in the examinee by quickly receiving a response from the examinee upon the occurrence of an error.

<Feedback on Second Ophthalmic Examination Apparatus>

When the examinee who needed intervention in the examination by the ophthalmic examination apparatus 10 is waiting for an examination by the second ophthalmic examination apparatus 110, a case where similar intervention is also required in the examination by the second ophthalmic examination apparatus 110 is conceivable. Hence, various types of information obtained in the ophthalmic examination apparatus 10 may be transmitted directly, or indirectly, to the second ophthalmic examination apparatus 110. Consequently, the smooth conducting of the examination in the second ophthalmic examination apparatus 110 can be expected.

For example, if manual alignment was manually adjusted in the ophthalmic examination apparatus 10, a parameter being an alignment adjustment result by the manual alignment in the ophthalmic examination apparatus 10 may be transmitted to the second ophthalmic examination apparatus 110 (a second transmission step). Upon the alignment in the second ophthalmic examination apparatus 110, alignment may be guided on the basis of the above-mentioned parameter. For example, an alignment target position may be set on the basis of the above-mentioned parameter. A target (reticle) presenting a target position may be displayed on an observation image upon the manual alignment in the second ophthalmic examination apparatus 110. Moreover, an alignment state of the target position in the second ophthalmic examination apparatus 110 may be adjusted automatically.

Moreover, for example, information indicating the type of error in the ophthalmic examination apparatus 10 may be transmitted to the second ophthalmic examination apparatus 110 (a third transmission step). At the start of the examination in the second ophthalmic examination apparatus 110, the second ophthalmic examination apparatus 110 that has received the information indicating the type of error may send a notice of the information on the type of error. The information on the type of error may be, for example, information indicating the content of assistance necessary for the examinee. Consequently, for example, the operator near the second ophthalmic examination apparatus 110 can proceed smoothly with the examination in the second ophthalmic examination apparatus 110 while giving necessary assistance.

<Change of Examination Order>

If an examination for one examinee is prolonged due to the occurrence of an error in the case of the occurrence of the error, it is conceivable that influences such as an increase in the examination waiting time of another examinee and congested examinations are caused. In other words, the examination efficiency for all examination targets may be reduced.

In contrast, as described above, in the embodiment, the management apparatus 120 may manage examination orders in such a manner as to associate the examination orders with the above-mentioned examinee (the examinee who underwent the examination by the ophthalmic examination apparatus 10 where the error occurred) and another examinee, respectively. The examination order here indicates the order to undergo examinations in a series of examinations including the examination by the ophthalmic examination apparatus 10 (a first examination) and a second examination (an examination different from the first examination).

If an error occurs in the examination by the ophthalmic examination apparatus 10, then the management apparatus 120 may change the examination order associated with the examinee or the other examinee on the basis of the handling method selection input in the selection step. Consequently, even if an error occurs, a reduction in examination efficiency in the facility is prevented.

Figure 6:
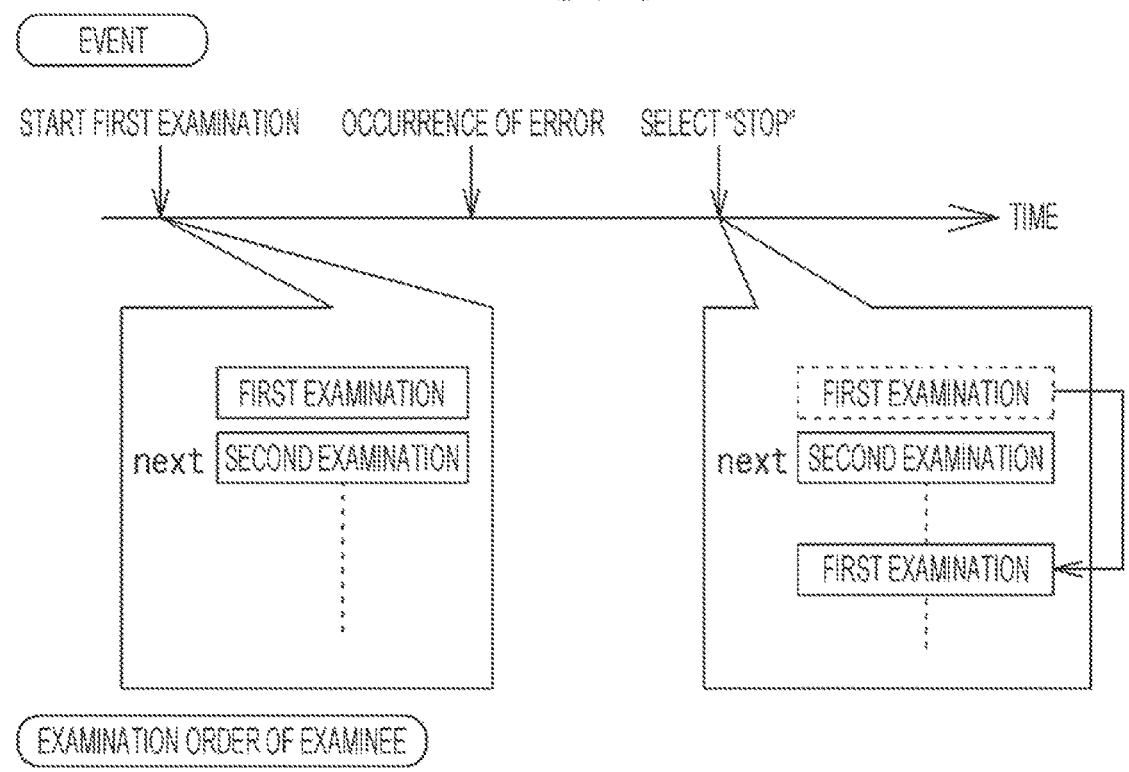
FIG. 6 is a diagram explaining an example of a change step in a management apparatus.

As one specific example, if a handling method of stopping that stops the examination by the ophthalmic examination apparatus 10 and guides the examinee to another examination is selected in the response step, the management apparatus 120 may change at least the examination order of the examinee on the basis of the handling method selection input in the examiner-side apparatus 20. For example, the examination order is adjusted in such a manner that a reexamination by the ophthalmic examination apparatus 10 is conducted after another examination (the second examination) as illustrated in FIG. 6. It is desirable that the second examination be an examination where an error similar to the error that occurred in the ophthalmic examination apparatus 10 is impossible to occur.

Figure 7:
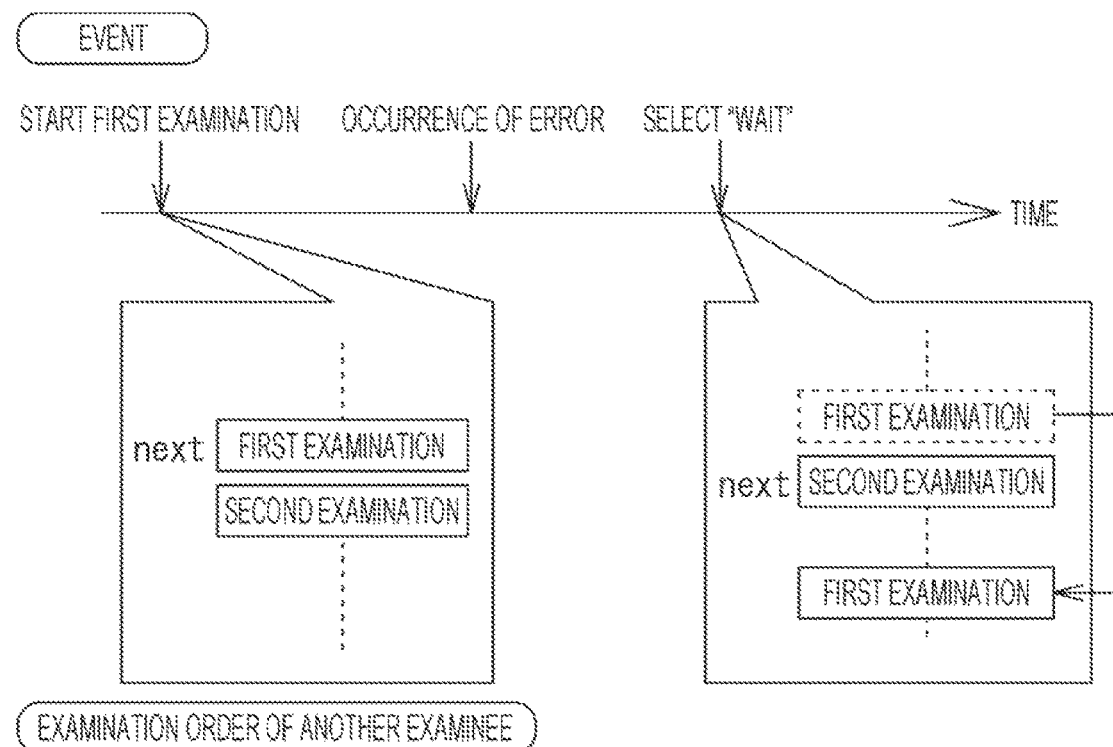
FIG. 7 is a diagram explaining another example of the change step in the management apparatus.

Moreover, as another specific example, if a handling method of waiting is selected in the ophthalmic examination apparatus 10 in the response step, the management apparatus 120 may change at least the examination order of the other examinee on the basis of the handling method selection input in the examiner-side apparatus 20. For example, if examination items scheduled for the other examinee include the examination by the ophthalmic examination apparatus 10, the examination order may be changed to set the examination by the ophthalmic examination apparatus 10 to a later time, considering a delay in the examination time of the examinee before the other examinee caused by the above-mentioned wait as illustrated in FIG. 7.

Moreover, the examination order managed in the management apparatus 120 may be adjusted in such a manner that the examination by the second ophthalmic examination apparatus 110 is conducted immediately after the examination by the first ophthalmic examination apparatus 10.

Up to this point the present disclosure has been described on the basis of the embodiment. However, the present disclosure can be variously modified.

<Timeout Process after Occurrence of Error>

For example, the handling methods of the above embodiment are always selected on the basis of the selection operation by the examiner. However, the selection is not necessarily limited to this. A case where the examiner is working on another task, and therefore can perform no operation on the examiner-side apparatus 20 for a while even if being notified of the occurrence of an error is also conceivable.

In contrast, for example, if the selection operation is not performed for a predetermined period of time after the notification of the occurrence of an error, a timeout process that the examiner-side apparatus 20 (or the ophthalmic examination apparatus 10) automatically selects any of predetermined handling methods from the plurality of handling methods may be executed.

The handling method that is selected by the timeout process may be the handling method of stopping. In other words, the examination may be stopped to output guidance information for guiding an examinee to the next examination (second examination) via the output device. Moreover, if a handling method is selected automatically by the timeout process as described above, information indicating that the timeout process has been performed may be displayed on the monitor of the examiner-side apparatus 20.

Moreover, the handling method that is selected by the timeout process may be a handling method of contact with an operator. In this case, information indicating the occurrence of an error in the ophthalmic examination apparatus 10 (and information indicating the content of the error) may be transmitted to the terminal apparatus 130. Consequently, the operator may be requested to take an action against the error that has occurred in the ophthalmic examination apparatus 10.

Such a timeout process as described above reduces the waiting time of the examinee after the occurrence of the error. As a result, for example, a reduction in examination efficiency in the facility is prevented.

<Application to Master-Slave System>

For example, the ophthalmic examination apparatus 10 can conduct an examination in a stand-alone manner in the ophthalmic examination system 1 of the above embodiment. However, the examination method is not necessarily limited to this. The ophthalmic examination apparatus 10 may be always controlled by an external master (a computer such as the examiner-side apparatus 20). In other words, the ophthalmic examination apparatus 10 may be a slave machine that does not support an examination in a stand-alone manner. For example, if the examiner-side apparatus 20 controls the ophthalmic examination apparatus 10 as a master, the steps illustrated in FIG. 4 are executed in the examiner-side apparatus 20. At this point in time, the steps related to the transmission and receipt of signals (S3, S4, S11, and S14) can be omitted in various steps illustrated in FIG. 4.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A method for an ophthalmic examination by an ophthalmic examination system including an ophthalmic examination apparatus and an examiner-side apparatus that is connected to the ophthalmic examination apparatus by a network and is provided with an interface for input/output, the method comprising:

a transmission step of transmitting an error signal from the ophthalmic examination apparatus to the examiner-side apparatus upon occurrence of an error in the ophthalmic examination apparatus;

a selection step of, upon the examiner-side apparatus receiving the error signal, notifying an examiner of the occurrence of the error via the interface and also accepting selection input for selecting any of a plurality of predetermined handling methods of the error;

a response step of the examiner-side apparatus transmitting a response signal to the ophthalmic examination apparatus on the basis of the selection input; and a notification step of, upon the ophthalmic examination apparatus receiving the response signal, notifying an examinee of guidance information on the action against the error on the basis of the response signal via an output device, wherein a handling method of stopping an examination that stops a first examination being an examination by the ophthalmic examination apparatus and guides the examinee to a second examination different from the first examination is included as one of the plurality of handling methods selectable in the response step, and upon the ophthalmic examination apparatus receiving the response signal related to the handling method of stopping the first examination, the first examination is stopped on the basis of the response signal, and the examinee is notified of guidance information for guiding the examinee to the second examination via the output device in the notification step.

2. The method for an ophthalmic examination according to claim 1, wherein
the ophthalmic examination system further includes a terminal apparatus that is placed in a same facility as the ophthalmic examination apparatus and connected to the network,
a handling method of a summons to an operator that summons an operator in the facility to the ophthalmic examination apparatus via the terminal apparatus is included as one of the plurality of handling methods selectable in the response step, and
the examiner-side apparatus transmits, to the terminal apparatus, a second response signal for summoning the operator upon the handling method of a summons to an operator being selected in the response step.

3. The method for an ophthalmic examination according to claim 1, wherein
the ophthalmic examination system further includes a management apparatus connected to the network,
the management apparatus manages examination orders in a series of examinations including the first examination by the ophthalmic examination apparatus and the second examination different from the first examination, associating the examination orders with the examinee and another examinee different from the examinee, respectively, and
the method further comprises a change step of the management apparatus changing the examination order associated with the examinee or the other examinee on the basis of the handling method selection input in the selection step.

4. The method for an ophthalmic examination according to claim 3, wherein
in the change step, at least the examination order of the examinee is changed on the basis of the selection input of the handling method of stopping in the response step.

5. The method for an ophthalmic examination according to claim 3, wherein
a handling method of waiting that makes the examinee to wait for a period of time from the occurrence of the error to manual operation of the ophthalmic examination apparatus is included as one of the plurality of handling methods selectable in the response step, and
in the change step, at least the examination order of the other examinee is changed on the basis of the selection input of the handling method of waiting in the response step.

6. The method for an ophthalmic examination according to claim 1, further comprising a timeout process step of automatically selecting any of predetermined handling methods automatically from the plurality of handling methods upon the examiner-side apparatus not accepting the selection input for a predetermined period of time after the receipt of the error signal.

7. The method for an ophthalmic examination according to claim 1, wherein in the response step, a video call is made between the ophthalmic examination apparatus and the examiner-side apparatus upon selecting the handling method.

8. The method for an ophthalmic examination according to claim 1, wherein
the error signal to be transmitted to the examiner-side apparatus in the transmission step includes information indicating a type of the error, and a content of a notification to be notified to the examiner via the interface in the selection step includes the information on the type of the error.

9. The method for an ophthalmic examination according to claim 1, wherein
the output device includes a display, and
the examinee is notified of the guidance information as visual information in the notification step.

10. A method for an ophthalmic examination by an ophthalmic examination system including an ophthalmic examination apparatus and an examiner-side apparatus that is connected to the ophthalmic examination apparatus by a network and is provided with an interface for input/output, the method comprising:
a transmission step of transmitting an error signal from the ophthalmic examination apparatus to the examiner-side apparatus upon occurrence of an error in the ophthalmic examination apparatus;
a selection step of, upon the examiner-side apparatus receiving the error signal, notifying an examiner of the occurrence of the error via the interface and also accepting selection input for selecting any of a plurality of predetermined handling methods of the error;
a response step of the examiner-side apparatus transmitting a response signal to the ophthalmic examination apparatus on the basis of the selection input; and
a notification step of, upon the ophthalmic examination apparatus receiving the response signal, notifying an examinee of guidance information on the action against the error on the basis of the response signal via an output device, wherein
a handling method of waiting that makes the examinee to wait for a period of time from the occurrence of the error to manual operation of the ophthalmic examination apparatus is included as one of the plurality of handling methods selectable in the response step, and
upon receiving the response signal related to the handling method of waiting, the ophthalmic examination apparatus notifies the examinee of guidance information for prompting the examinee to wait via the output device in the notification step,
the ophthalmic examination system further includes a second ophthalmic examination apparatus that is placed in a same facility as the ophthalmic examination apparatus and connected to the network, and
the method further comprises a second transmission step of transmitting, to the second ophthalmic examination apparatus, a parameter being an alignment adjustment result by manual alignment in the ophthalmic examination apparatus.

11. A method for an ophthalmic examination by an ophthalmic examination system including an ophthalmic examination apparatus and an examiner-side apparatus that is connected to the ophthalmic examination apparatus by a network and is provided with an interface for input/output, the method comprising:
a transmission step of transmitting an error signal from the ophthalmic examination apparatus to the examiner-side apparatus upon occurrence of an error in the ophthalmic examination apparatus;
a selection step of, upon the examiner-side apparatus receiving the error signal, notifying an examiner of the occurrence of the error via the interface and also accepting selection input for selecting any of a plurality of predetermined handling methods of the error;

a response step of the examiner-side apparatus transmitting a response signal to the ophthalmic examination apparatus on the basis of the selection input; and a notification step of, upon the ophthalmic examination apparatus receiving the response signal, notifying an examinee of guidance information on the action against the error on the basis of the response signal via an output device, wherein the ophthalmic examination system further includes a second ophthalmic examination apparatus that is placed in a same facility as the ophthalmic examination apparatus and connected to the network, and the method further comprises a third transmission step of transmitting, to the second ophthalmic examination apparatus, information indicating a type of the error.

* * * * *